US00PP14737P3

(12) United States Plant Patent
Wolfram

(10) Patent No.: US PP14,737 P3
(45) Date of Patent: Apr. 27, 2004

(54) PRUNUS TREE ROOTSTOCK NAMED 'PIKU 1'

(50) Latin Name: *Prunus L.*
Varietal Denomination: Piku 1

(75) Inventor: Brigitte Wolfram, Dresden (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 0 days.

(21) Appl. No.: 10/136,465

(22) Filed: May 1, 2002

(65) Prior Publication Data

US 2003/0208807 P1 Nov. 6, 2003

(51) Int. Cl.[7] ..... A01H 5/00

(52) U.S. Cl. ..... Plt./183

(58) Field of Search ..... Plt./183

*Primary Examiner*—Bruce R. Campell
*Assistant Examiner*—Annette H. Para

(74) *Attorney, Agent, or Firm*—Webb, Ziesenheim Logsdon Orkin & Hanson, P.C.

(57) ABSTRACT

A new and distinct Prunus rootstock compatible with other Prunus varieties and producing trees with reduced growth, hardiness to frost and high productivity.

4 Drawing Sheets

Classification: *Prunus L.*
Varietal denomination: 'Piku 1'.

BACKGROUND OF THE INVENTION

The present invention comprises a new and distinct cultivar of hybrid Prunus known by the varietal name 'Piku 1'. The new variety was discovered in 1972 in a selective breeding program designed to produce growth reducing rootstock for cherry trees in Dresden-Pillnitz, Germany as a cross between an unnamed, unpatented variety of *Prunus avium* rootstock seedling (female parent) and an unnamed, unpatented Prunus hybrid of *Prunus canescens*×*Prunus tomentosa* (male parent). The new variety differs from its parents in its growth habit. The following characteristic distinguish the new variety from *Prunus avium* rootstock varieties:

1. Three-way hybrid.
2. Reduces growth in grafted varieties by 30%.
3. Precocious, about 1–3 years.
4. Higher productivity.
5. Propagated by green cuttings or tissue culture.
6. High resistance to winter frost.
7. Leaf margins roll inwards.

The new variety was first asexually reproduced via green cuttings and tissue culture in 1975 in Dresden-Pillnitz, Germany and subsequent propagation therein has confirmed that the characteristics of the new variety are stable and are transmitted to subsequent generations.

DESCRIPTION OF THE DRAWINGS

The accompanying photographic drawings illustrate the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via green cuttings and tissue culture carried out in Dresden-Pillnitz, Germany. The color designations were taken in outdoors Dresden-Pillnitz, Germany. Rootstocks were 6 to 7 years old when described. Color designations are noted with reference to standard *P. avium* rootstock. The new variety is adaptable to soil and is free of PNRV and PDV. As a rootstock, it can be reproduced via softwood cuttings and tissue culture. The new variety anchors well with few root sprouts, good compatibility with grafts and exhibits reduced growth.

TREE

Size: Medium; having an average height of 2.60 m and an average width of 1.90 m.
Form: Upright, broad.
Trunk:
- *Surface texture.*—Exfoliating.
- *Bark color.*—Middle brown to dark brown.
- *Diameter.*—7.0 cm, measured at a height of 40 cm.

Branches:
- *Surface texture.*—Smooth.
- *Bark color.*—166A to 200B; similar to a birch tree.
- *New growth color.*—Light-dark red.
- *Mature growth color.*—Dark brown.
- *Average crotch angle.*—45–50°.
- *Internode length.*—About 1.8 cm.
- *Lenticels.*—Diameter: 0.05–0.15 cm. Color: 160D. Amount per shoot: >100.
- *Bud.*—Small.

Leaves:
- *Length.*—9.1 cm.

*Width.*—4.0 cm.
*Surface texture.*—Fine, smooth.
*Form.*—Elongated, elliptical.
*Color.*—Upper Surface: 146A. Lower Surface: 146B.
*Margin.*—Rolls towards upper surface.

Petioles:
*Length.*—1.4 cm.
*Thickness.*—0.12 cm.

Leaf glands:
*Quantity.*—1–2.
*Position.*—On the end of the leaves.
*Size.*—0.15 cm.
*Color.*—Red-brown.

Stipules:
*Quantity.*—Rare.
*Length.*—1.0–1.5 cm.

Flowers:
*Diameter.*—2.50 cm.
*Color.*—Upper Surface: N155A. Lower Surface: N155A.
*Number.*—Many.
*Petals.*—Length: Approximately 1.2 cm. Width: Approximately 0.6 cm. Quantity per flower: 5.
*Sexual characteristics.*—Diploid.
*Stamen number.*—>10.
*Pistil number.*—1.

FRUIT

Maturity date/location: Early in Dresden, Pillnitz.
Size: Small; low crop yield.
Weight: 1–2 grams.
Axial diameter: 1–1.5 cm.
Fruit stone:
*Length.*—0.7 cm.
*Diameter.*—0.4 cm.
Skin: Thin, soft, colored 187A.
Flesh color: 187A.
Seeds: Surface color 159C/159D, having a smooth texture.

GENERAL

Weather hardiness: Tolerant to winter frost.
Disease resistance: Tolerant to Cytospora.

I claim:

1. A new and distinct variety of Prunus rootstock named 'Piku 1' substantially as shown and described.

* * * * *

UNITED STATES PATENT AND TRADEMARK OFFICE

CERTIFICATE OF CORRECTION

Figure 1:
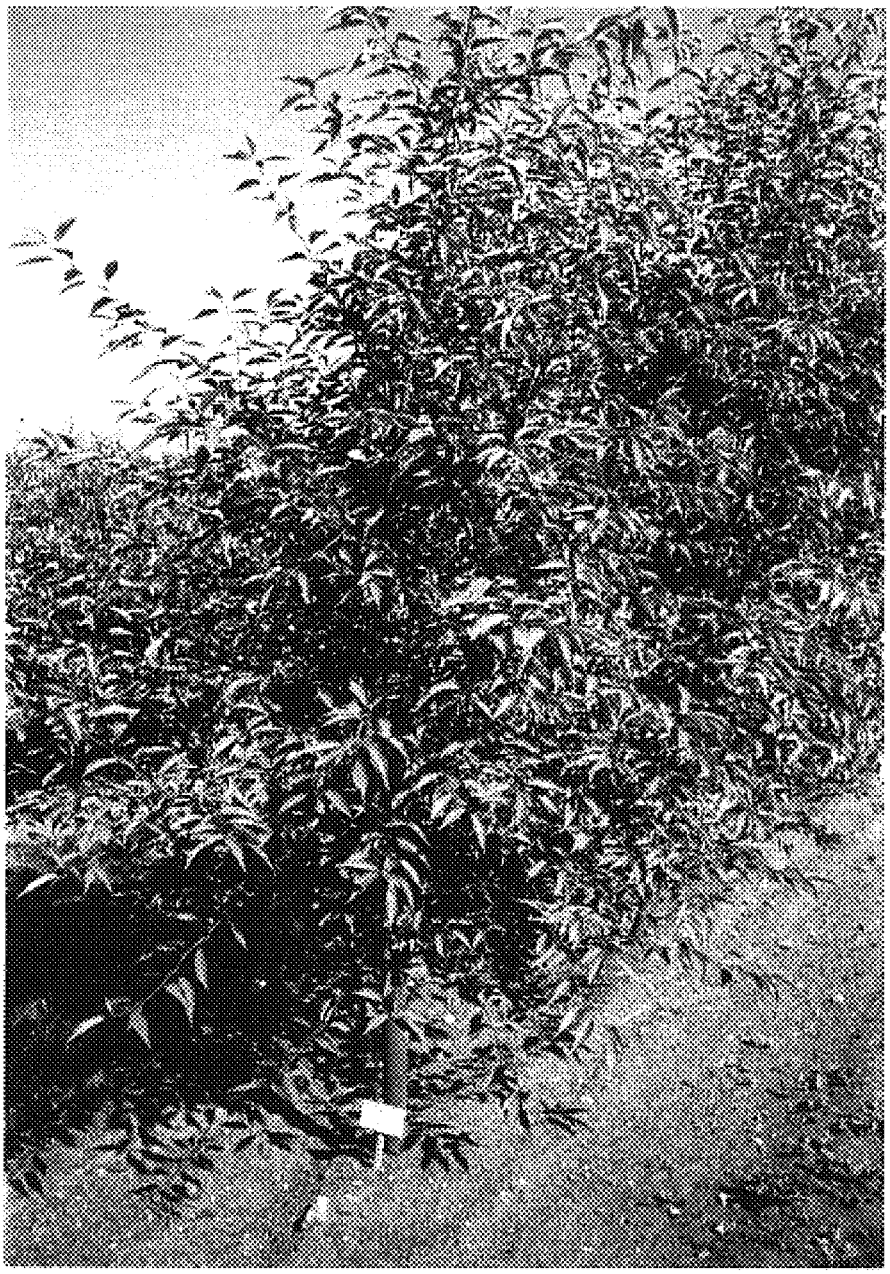
FIG. 1 shows the tree of the new variety.
Figure 2:
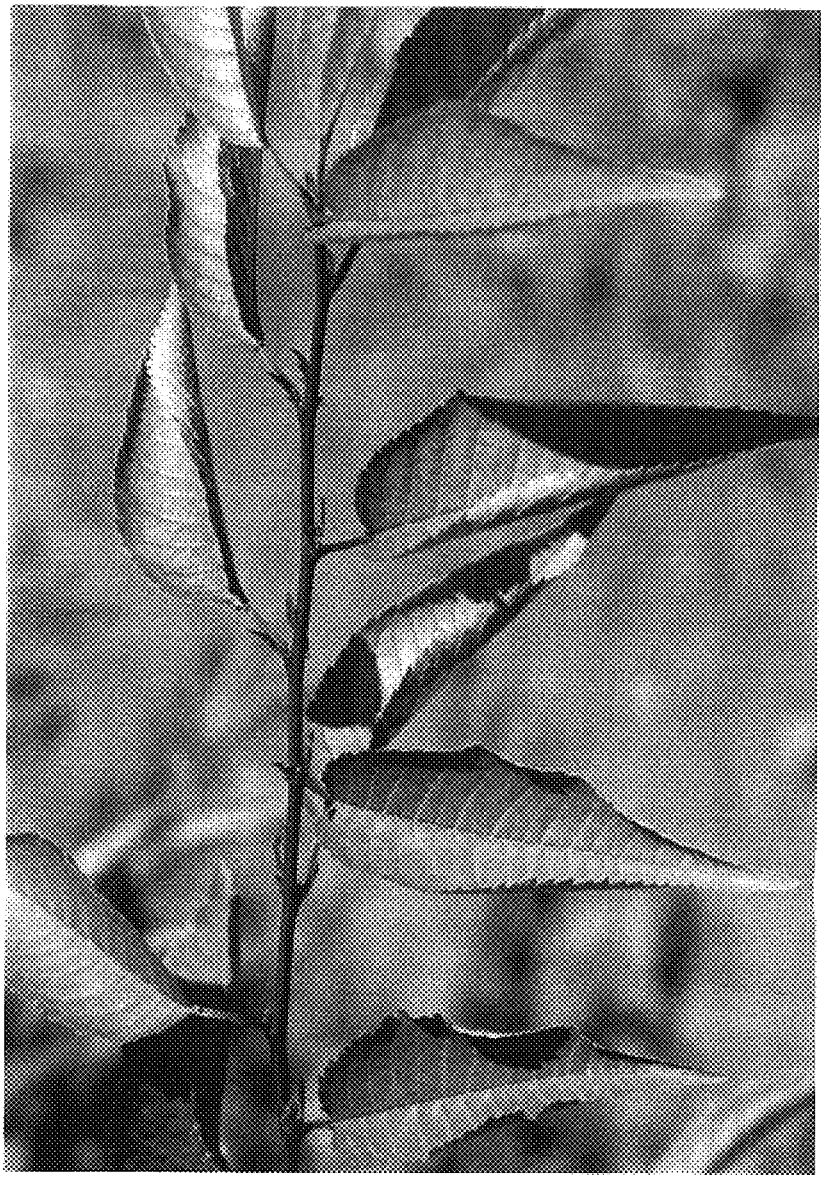
FIG. 2 shows a branch with leaves.
Figure 3:
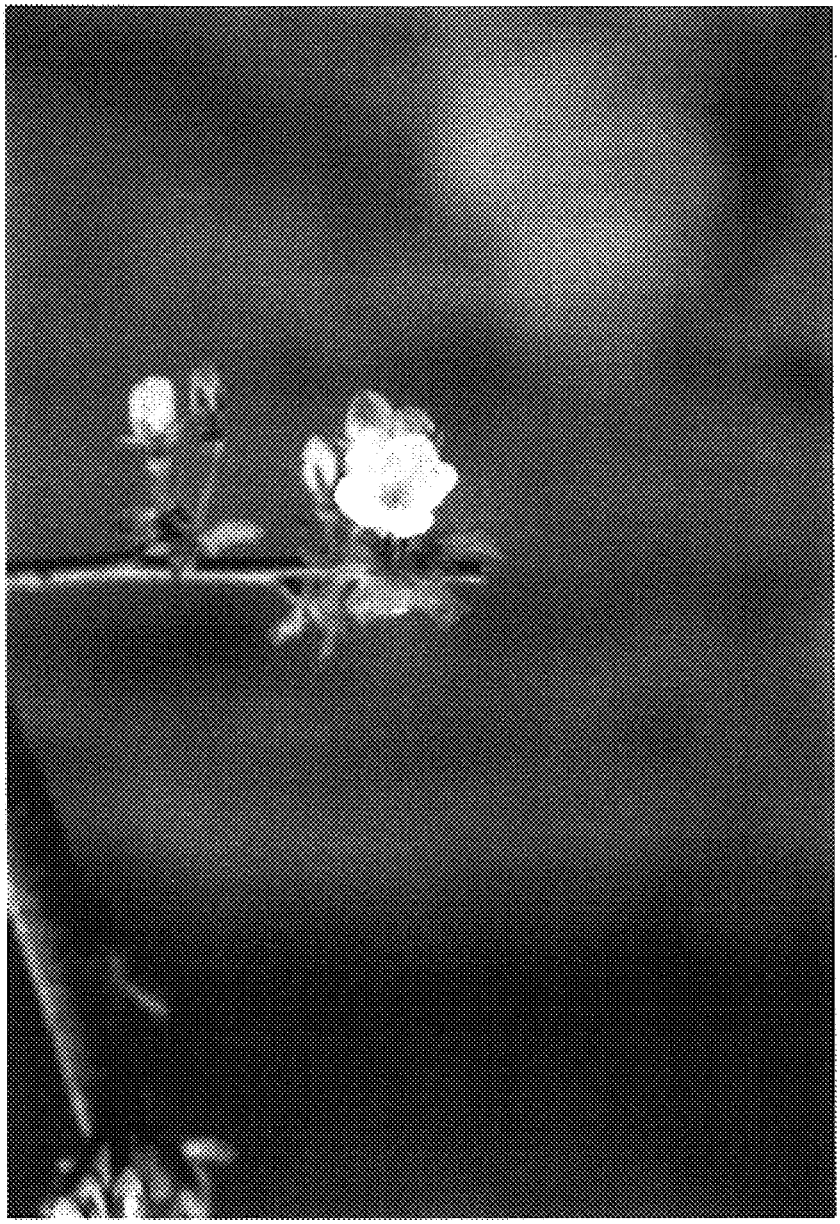
FIG. 3 shows a branch with flower buds.
Figure 4:
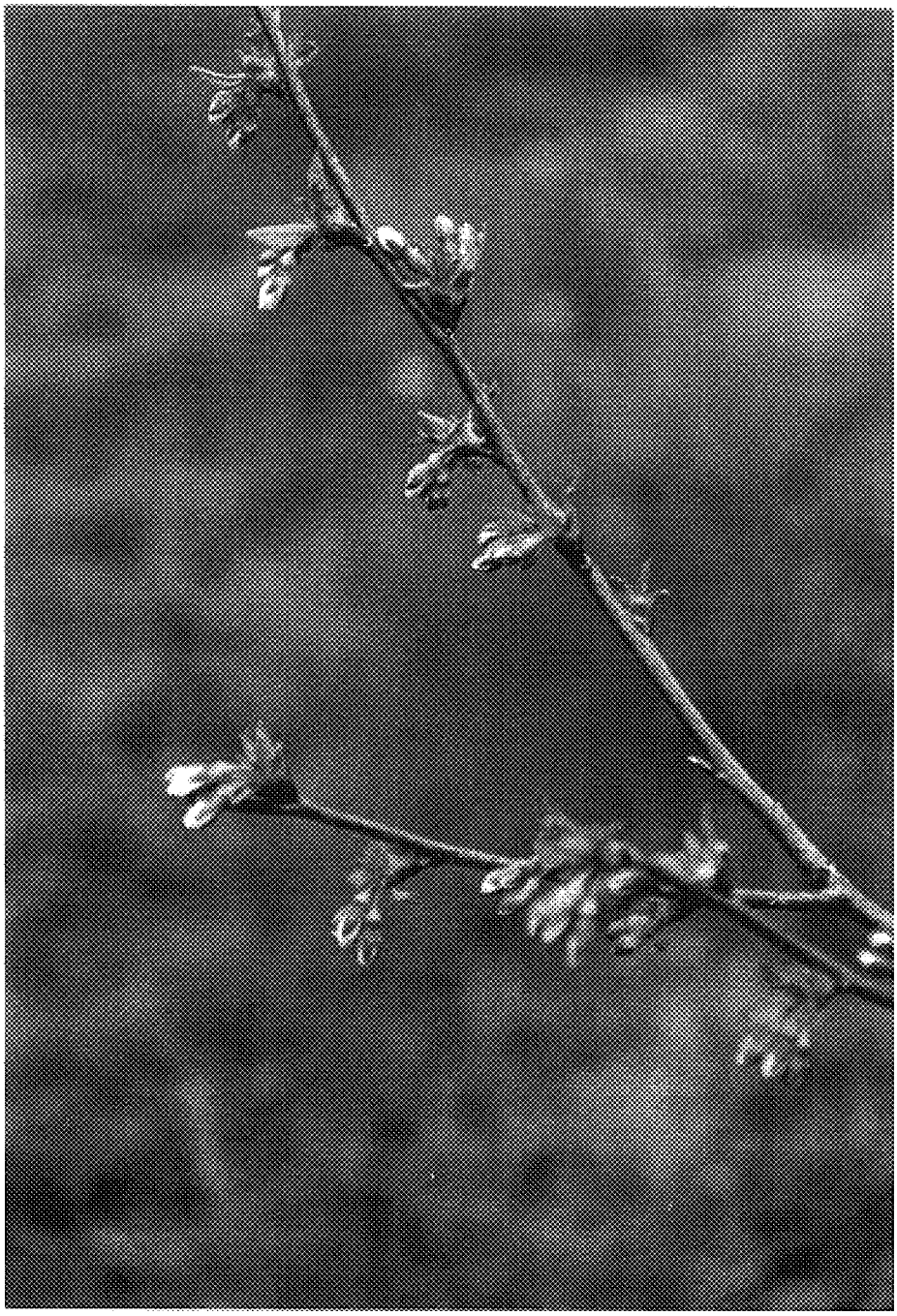
FIG. 4 shows a branch with opened flowers.
Figure 3:
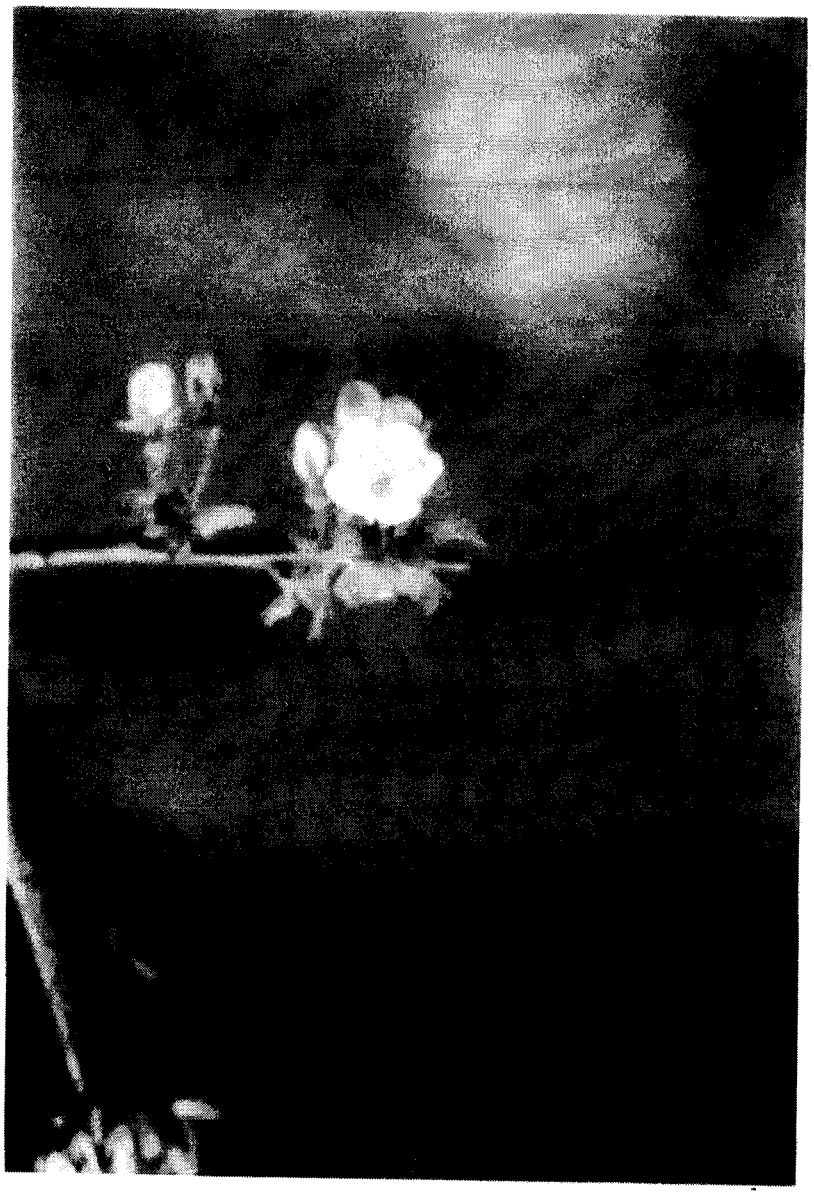
Figure 4:
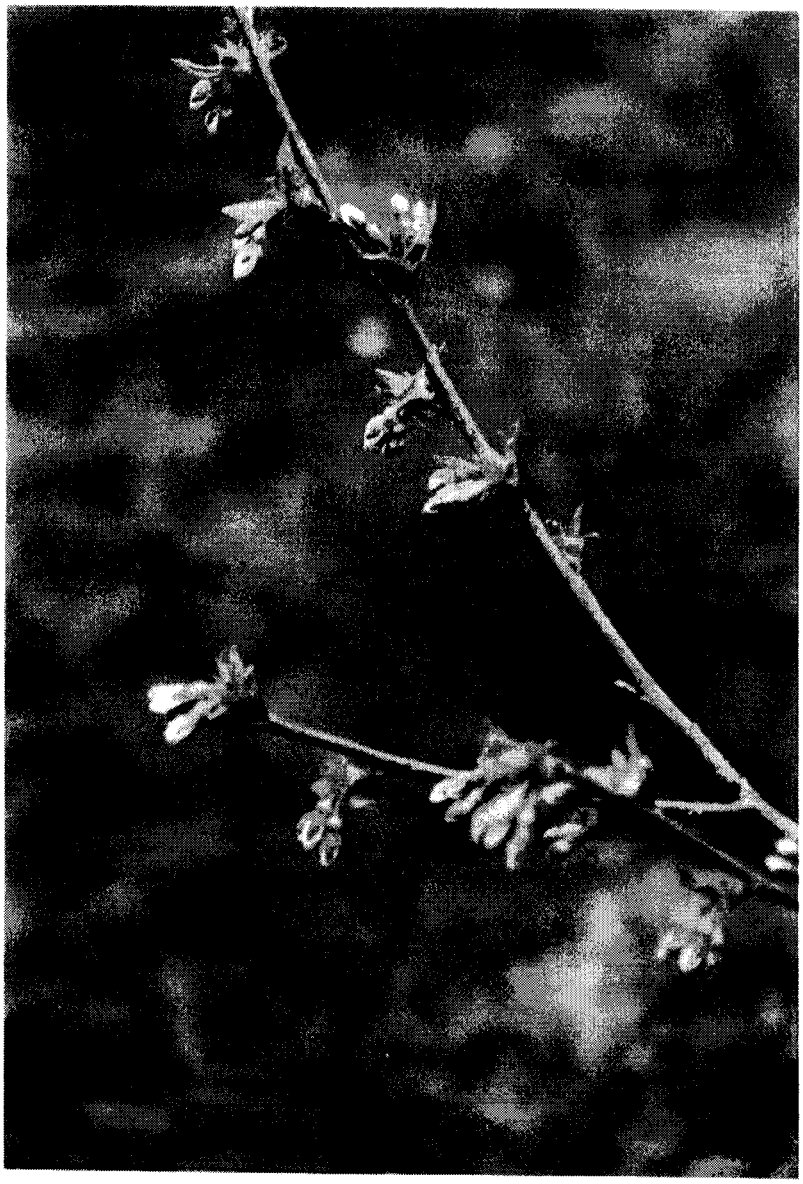

PATENT NO. : PP14,737 P3
APPLICATION NO. : 10/136465
DATED : April 27, 2004
INVENTOR(S) : Brigitte Wolfram It is certified that error appears in the above-identified patent and that said Letters Patent is hereby corrected as shown below:

The sheets of drawings consisting of figures 3 and figure 4, should be deleted to appear as per attached figures 3 and 4.

Signed and Sealed this
Twelfth Day of April, 2011

David J. Kappos

David J. Kappos
*Director of the United States Patent and Trademark Office*